(12) United States Patent
Kiderman et al.

(10) Patent No.: US 8,585,609 B2
(45) Date of Patent: Nov. 19, 2013

(54) QUANTITATIVE, NON-INVASIVE, CLINICAL DIAGNOSIS OF TRAUMATIC BRAIN INJURY USING SIMULATED DISTANCE VISUAL STIMULUS DEVICE FOR NEUROLOGIC TESTING

(75) Inventors: Alexander D Kiderman, Pittsburgh, PA (US); Howison Schroeder, Pittsburgh, PA (US); Thomas Joos, Pittsburgh, PA (US); Greg Frank, Pittsburgh, PA (US)

(73) Assignee: Neuro Kinetics, Inc., Pittsburgh, PA (US)

( * ) Notice: Subject to any disclaimer, the term of this patent is extended or adjusted under 35 U.S.C. 154(b) by 632 days.

(21) Appl. No.: 12/577,143

(22) Filed: Oct. 9, 2009

(65) Prior Publication Data

US 2010/0094161 A1    Apr. 15, 2010

Related U.S. Application Data

(60) Provisional application No. 61/104,133, filed on Oct. 9, 2008.

(51) Int. Cl.
*A61B 5/00* (2006.01)

(52) U.S. Cl.
USPC .......................................... 600/558

(58) Field of Classification Search
USPC ............................... 600/558, 587
See application file for complete search history.

(56) References Cited

U.S. PATENT DOCUMENTS

| | | |
|---|---|---|
| 3,612,642 A | 10/1971 | Dostal |
| 4,006,974 A | 2/1977 | Resnick |
| 4,084,182 A | 4/1978 | Maiman |
| 4,309,608 A | 1/1982 | Adamson |
| 4,320,768 A | 3/1982 | Ledley et al. |
| 4,474,186 A | 10/1984 | Ledley et al. |
| 4,572,199 A | 2/1986 | LaCourse |
| 4,836,219 A | 6/1989 | Hobson et al. |
| 4,852,988 A | 8/1989 | Velez et al. |
| 4,863,259 A | 9/1989 | Schneider et al. |
| 5,070,883 A | 12/1991 | Kasahara |
| 5,098,426 A | 3/1992 | Sklar et al. |

(Continued)

FOREIGN PATENT DOCUMENTS

JP    11/184621    7/1999

OTHER PUBLICATIONS

Jason S. Babcock, Jeff B. Pelz, Building a lightweight eyetracker, http://www.cis.rit.edu/people/faculty/pelz/publications/ETRA04$_{13}$ babcock_pelz.pdf, 2004.

(Continued)

*Primary Examiner* — Max Hindenburg
(74) *Attorney, Agent, or Firm* — Blynn L. Shideler; Krisanne Shideler; BLK Law Group

(57) ABSTRACT

A portable virtual reality device is disclosed that will facilitate the effective and efficient screening for TBI in military personnel in forward deployed military settings or remote locations using minimally trained staff. This includes the establishment of a protocol that will provide cost effective pre-screening of military personnel prior to deployment to establish a baseline of brain function prior to possible future injury. The efficiency of the device will promote subsequent follow-up screening to assess the effectiveness of prescribed TBI treatment. Further protocols for diagnosis and rehabilitation applications using the same virtual reality portable device will allow more advanced usage for clinicians providing ongoing evaluation and treatment.

20 Claims, 1 Drawing Sheet

(56) References Cited

U.S. PATENT DOCUMENTS

| | | | |
|---|---|---|---|
| 5,130,838 | A | 7/1992 | Tanaka et al. |
| 5,252,999 | A | 10/1993 | Sukigara et al. |
| 5,304,112 | A | 4/1994 | Mrklas et al. |
| 5,305,746 | A | 4/1994 | Fendrock |
| 5,320,109 | A | 6/1994 | Chamoun et al. |
| 5,345,281 | A | 9/1994 | Taboada et al. |
| 5,365,941 | A | 11/1994 | Yoshimatsu |
| 5,368,041 | A | 11/1994 | Shambroom |
| 5,381,804 | A | 1/1995 | Shambroom |
| 5,410,376 | A | 4/1995 | Cornsweet et al. |
| 5,458,117 | A | 10/1995 | Chamoun et al. |
| 5,481,622 | A | 1/1996 | Gerhardt |
| 5,491,492 | A | 2/1996 | Knapp |
| 5,652,756 | A | 7/1997 | Stultz et al. |
| 5,687,020 | A | 11/1997 | Park et al. |
| 5,704,369 | A | 1/1998 | Scinto |
| 5,714,967 | A | 2/1998 | Okamura et al. |
| 5,792,069 | A | 8/1998 | Greenwald et al. |
| 5,813,404 | A | 9/1998 | Devlin et al. |
| 5,821,521 | A | 10/1998 | Bridgelall et al. |
| 5,838,420 | A | 11/1998 | MacGregor Donaldson |
| 5,877,732 | A * | 3/1999 | Ziarati ........................ 345/8 |
| 5,892,566 | A | 4/1999 | Bullwinkel |
| 5,942,954 | A | 8/1999 | Galiana |
| 5,943,116 | A | 8/1999 | Zeimer |
| 5,963,300 | A | 10/1999 | Horwitz |
| 5,980,513 | A | 11/1999 | Frey et al. |
| 5,983,128 | A | 11/1999 | Baudonniere |
| 6,003,991 | A | 12/1999 | Virre |
| 6,024,707 | A | 2/2000 | Scinto |
| 6,032,064 | A | 2/2000 | Devlin et al. |
| 6,032,072 | A | 2/2000 | Greenwald et al. |
| 6,033,073 | A | 3/2000 | Potapova |
| 6,077,237 | A | 6/2000 | Campbell |
| 6,089,716 | A | 7/2000 | Lashkari et al. |
| 6,090,051 | A | 7/2000 | Marshall |
| 6,099,124 | A | 8/2000 | Hidaji |
| 6,113,237 | A | 9/2000 | Ober |
| 6,120,461 | A | 9/2000 | Smyth |
| 6,162,186 | A | 12/2000 | Scinto |
| 6,213,943 | B1 | 4/2001 | Abreu |
| 6,231,187 | B1 | 5/2001 | Munoz |
| 6,247,813 | B1 | 6/2001 | Kim et al. |
| 6,271,915 | B1 | 8/2001 | Frey et al. |
| 6,275,718 | B1 | 8/2001 | Lempert |
| 6,299,308 | B1 | 10/2001 | Veronka et al. |
| 6,367,932 | B1 | 4/2002 | Donaldson |
| 6,402,320 | B1 | 6/2002 | Borchert |
| 6,456,261 | B1 | 9/2002 | Zhang |
| 6,459,446 | B1 | 10/2002 | Harman |
| 6,467,905 | B1 | 10/2002 | Stahl |
| 6,524,581 | B1 | 2/2003 | Adamis |
| 6,542,081 | B2 | 4/2003 | Torch |
| 6,551,575 | B1 | 4/2003 | Greenspan |
| 6,568,808 | B2 | 5/2003 | Campin |
| 6,574,352 | B1 | 6/2003 | Skolmoski |
| 6,609,523 | B1 | 8/2003 | Anthony |
| 6,629,935 | B1 | 10/2003 | Miller |
| 6,631,989 | B2 | 10/2003 | Odom et al. |
| 6,634,749 | B1 | 10/2003 | Morrison et al. |
| 6,637,883 | B1 | 10/2003 | Tengshe |
| 6,652,458 | B2 | 11/2003 | Blazey |
| 6,659,611 | B2 | 12/2003 | Amir et al. |
| 6,669,341 | B2 | 12/2003 | Wirth |
| 6,697,894 | B1 | 2/2004 | Mitchell et al. |
| 6,748,275 | B2 | 6/2004 | Lattner |
| 6,796,947 | B2 | 9/2004 | Watt |
| 6,800,062 | B2 | 10/2004 | Epley |
| RE38,668 | E | 12/2004 | Edwards |
| 6,943,754 | B2 | 9/2005 | Aughey et al. |
| 7,115,099 | B2 * | 10/2006 | Miller et al. ................ 600/558 |
| 7,448,751 | B2 | 11/2008 | Kiderman et al. |
| 7,520,614 | B2 | 4/2009 | Joos et al. |
| 7,651,224 | B2 | 1/2010 | Wood et al. |
| 7,665,845 | B2 | 2/2010 | Kiderman et al. |
| 7,819,818 | B2 * | 10/2010 | Ghajar ........................ 600/558 |
| 7,988,287 | B1 * | 8/2011 | Butler et al. ................ 351/210 |
| 8,333,472 | B2 * | 12/2012 | Kiderman .................... 351/200 |
| 2002/0027779 | A1 | 3/2002 | Cassarly |
| 2002/0085174 | A1 | 7/2002 | Bolger |
| 2002/0171805 | A1 | 11/2002 | Odom et al. |
| 2002/0175880 | A1 | 11/2002 | Melville |
| 2003/0028081 | A1 | 2/2003 | Blazey |
| 2004/0181168 | A1 | 9/2004 | Plant |
| 2005/0024586 | A1 | 2/2005 | Teiwes |
| 2005/0079636 | A1 | 4/2005 | White |
| 2005/0099601 | A1 | 5/2005 | MacDougall et al. |
| 2005/0101877 | A1 | 5/2005 | Miller |
| 2005/0110950 | A1 | 5/2005 | Thorpe |
| 2005/0216243 | A1 | 9/2005 | Graham |
| 2006/0098087 | A1 | 5/2006 | Brandt et al. |
| 2006/0235331 | A1 | 10/2006 | Kiderman |
| 2007/0132841 | A1 | 6/2007 | MacDougall et al. |
| 2008/0273084 | A1 | 11/2008 | MacDougall et al. |
| 2008/0278685 | A1 | 11/2008 | MacDougall et al. |

OTHER PUBLICATIONS

D. Zhu et al., Computer Methods and Programs in Biomedicine 59 (1999), pp. 146-157.

* cited by examiner

QUANTITATIVE, NON-INVASIVE, CLINICAL DIAGNOSIS OF TRAUMATIC BRAIN INJURY USING SIMULATED DISTANCE VISUAL STIMULUS DEVICE FOR NEUROLOGIC TESTING

RELATED APPLICATIONS

This application claims the benefit of U.S. Provisional patent application Ser. No. 61/104,133 filed Oct. 9, 2008 entitled "Quantitative, Non-Invasive, Clinical Diagnosis of Traumatic Brain Injury."

BACKGROUND OF THE INVENTION

1. Field of the Invention

The present invention relates to Traumatic Brain Injury (TBI or mTBI) and psychological health, and more specifically to quantitative, non-invasive, clinical diagnosis of traumatic brain injury, particularly for military applications.

2. Background Information

Military personnel, despite using strong protective devices, frequently suffer blast injuries to the head. In a study conducted at the Walter Reed Army Medical Center, 62% of Operation Iraqi Freedom combat wounded troops showed symptoms of mild to severe brain injuries (Collectively TBI). Of these, 91.6% had possibly sustained a TBI injury as a result of a blast. A number of recent studies have substantiated the presence of vestibular deficits in the acute period following TBI.

Proper treatment of TBI injury requires an accurate diagnosis of the structures affected. Proper treatment of TBI injury requires an accurate diagnosis of the structures affected. The mechanisms of injury in TBI cause a variety of abnormalities in the peripheral vestibular mechanisms, central vestibular structures, ocular-motor tracts, cerebellum, as well as all portions of the brain communicating with these structures. The onset of vestibular deficits generally occurs within seven to ten days post injury. While reported symptoms of dizziness resolve after three months, 15% have persistent symptoms one year later.

Existing screening and diagnostic tools employed on patients with balance and neurological disorders associated with TBI based on the traditional battery of vestibular, balance and neurological tests requires the use of large stationary systems (neuro-otologic test center, Barany/rotary chair, ENG/VNG, computerized posturography/balance platforms, etc.). These large systems deploy a full battery of ocular motor, motion, artificial motion, balance and combined tests. Utilizing such devices may be practical in hospital settings, but are not useful in forward deployed military settings, or remote locations, such as first responder emergency medical technicians (EMTs).

It is the object of the present invention to address the deficiencies of the prior art.

SUMMARY OF THE INVENTION

The present invention is drawn to the development of a portable virtual reality device that will facilitate the effective and efficient screening for TBI in subjects such as military personnel in forward deployed military settings or remote locations using minimally trained staff.

One aspect of the invention provides a method of diagnosis of traumatic brain injury comprising the steps of: providing a stimulus generating eye tracking unit, such as a head mounted goggle based eye tracking unit coupled to the subject; presenting a plurality of virtual reality based visual stimulus to the subject, wherein at least one visual stimulus is at a simulated distance in the eye tracking unit, wherein each visual stimulus provides a target stimulus for a visual based neurologic test; obtaining objective physiologic response of the subject from the eye tracking unit based upon each of neurologic test associated with each visual stimulus presented to the subject; and using the objective physiologic responses to the neurologic tests to diagnose the presence of traumatic brain injury.

The method of diagnosis of traumatic brain injury according to the invention may provide that the visual stimulus presented to the subject includes nystagmus tests, such as at least one horizontal nystagmus test, one vertical and one spontaneous nystagmus test. The visual stimulus presented to the subject may include at least one horizontal smooth pursuit test and at least one vertical smooth pursuit test. The visual stimulus presented to the subject may include at least one horizontal saccades test and at least one vertical saccades test.

The step of using the objective physiologic responses to diagnose the presence of traumatic brain injury may include determining whether at least one post-trauma objective physiologic responses of the subject differs from an associated objective physiologic response of a normative database of similar subjects by greater than a preset threshold for that response. The method of diagnosis of traumatic brain injury according to invention may further include the step of obtaining pre-trauma objective physiologic responses of the subject from the head mounted goggle unit based upon each of the visual stimulus presented to the subject, wherein the pre-trauma objective physiologic responses form a baseline for the subject.

One implementation of the present invention includes the establishment of a protocol that will provide cost effective pre-screening of military personnel prior to deployment to establish a baseline of brain function prior to possible future injury. The efficiency of the device will promote subsequent follow-up screening to assess the effectiveness of prescribed TBI treatment. Further protocols for diagnosis and rehabilitation applications using the same virtual reality portable device will allow more advanced usage for clinicians providing ongoing evaluation and treatment.

The present invention provides a simple, quantitative, non-invasive method to diagnose TBI or mTBI that can be used for deployed troops; efficient clinical diagnostic criteria methodologies for detecting TBI, while distinguishing it from psychological co-morbidities; Innovative therapies for TBI; and an impact on rehabilitation strategies on neural plasticity and neurogenesis following TBI.

These and other advantages of the present invention will be clarified in the description of the preferred embodiments.

DESCRIPTION OF THE PREFERRED EMBODIMENTS

Figure 1:
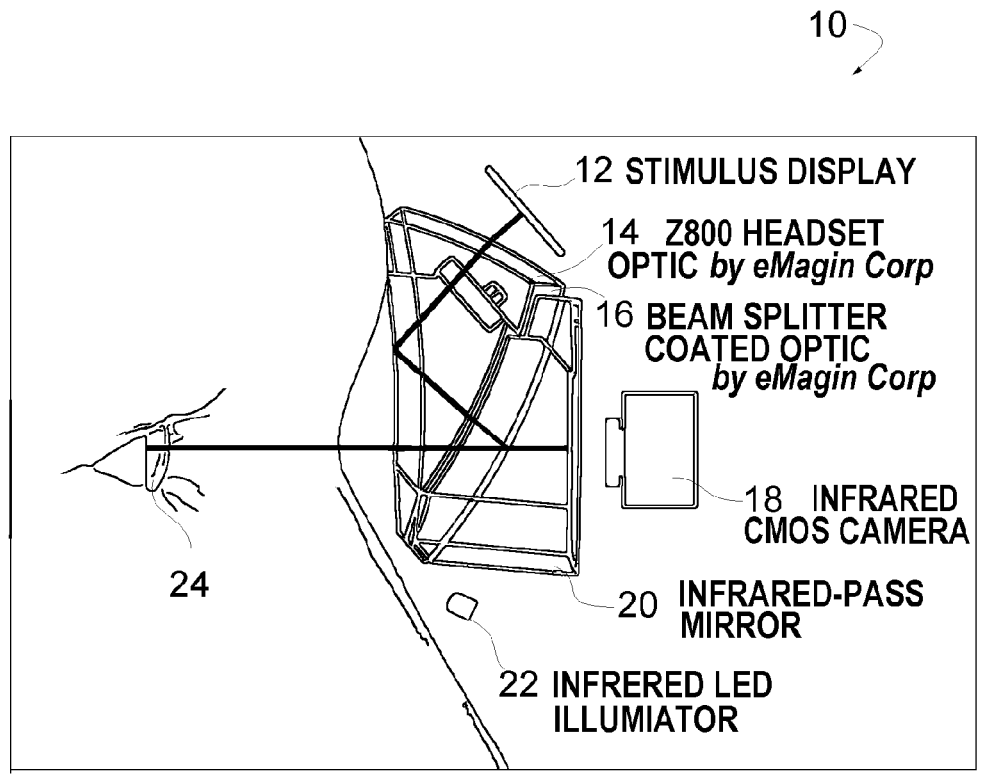
FIG. 1 schematically illustrates a portable virtual reality device that will facilitate the effective and efficient screening for TBI in accordance with the present invention.
Figure 2:
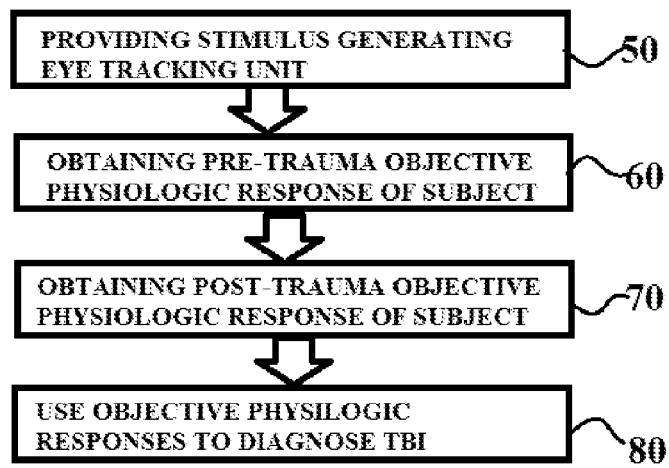
FIG. 2 schematically illustrates a method of using the portable virtual reality device of FIG. 1 that facilitates the effective and efficient screening for TBI in accordance with the present invention.

It is noted that, as used in this specification and the appended claims, the singular forms "a," "an," and "the" include plural referents unless expressly and unequivocally limited to one referent.

The method of diagnosis of traumatic brain injury according to one aspect of the invention comprising the steps of: providing at step 50 a stimulus generating eye tracking unit 10, such as a head mounted goggle based eye tracking unit that can present virtual reality based visual targets to the subject. The unit 10 coupled to the subject; presenting a plurality of virtual reality based visual stimulus to the subject, wherein at least one visual stimulus is at a simulated distance in the eye tracking unit, wherein each visual stimulus provides a target stimulus for a visual based neurologic test; obtaining at step 70 objective physiologic response of the subject from the eye tracking unit based upon each of neurologic test associated with each visual stimulus presented to the subject; and using the objective physiologic responses to the neurologic tests to diagnose at step 80 the presence of traumatic brain injury.

Virtual environment exposure, also called virtual reality or VR, has proven highly efficient and effective in vestibular rehabilitation since the experience gained during VR exposure is transferable to the real world.

The VR technology in the present invention is used to accurately provide a simulated distance to a visual target for performing a variety of standard neurologic tests on the subject.

Additionally, the VR use in the rehabilitation of TBI accelerates the compensation of an acute loss of peripheral or central vestibular function by improving adaptive modifications of the vestibulo-ocular reflex. This device has the substantial and tremendous potential of being used bedside and in the home to increase rehabilitation compensation speed and degree.

Innovations of this portable device include: Efficient pre-screening of military personnel. Immediate post-accident screening of soldiers for TBI or mTBI in forward deployed areas of operation. Follow-up screening for assessing prescribed TBI or mTBI treatment. Use as a portable rehabilitation tool for mTBI patients.

The device provides Combined VR and visual stimulus with eye tracking technology in portable package. Remote data access from forward deployed facilities to other medical personnel for triage can be implemented.

Current development in 3-D and VR has produced continuous breakthroughs in the areas of science, medicine and military applications. At the heart of VR is the accelerated 3-D graphics hardware that has been doubling in performance every six months. The cost of PC hardware has also continued to decline. In the area of VR software, the landscape has greatly improved with new tools, web integration and a general acceptance of the new technology. New display technology aids VR in the areas of projection, screen technology and micro displays for head-mounted displays. New OLED micro displays are low power, easy to view, and compact. These improvements allow for a goggle based VR that can produce moving visual stimulus at simulated distances for a variety of neurologic tests of the present invention.

The FIGURE is a schematic design of VRETG that includes the head-mounted goggles with the built-in 940 nm infrared micro LED 22 for illumination of the eyes 24 and the beam splitter plastic coated optic 14 that reflects visible light from OLED micro display 12. The setup allows reflected IR light from the eyes to be sent directly to the eye tracking miniature digital cameras 20 behind the mirrors 20. Simply, the VR screen provides the visual stimulus and the cameras capture eye response for quick analysis and triage.

The details of the VR display are believed to be known to those or ordinary skill in the art and it allows the system to present visual images or targets to the user that have a perceived or simulated distance much greater than the actual distance in the goggles. As a simple example the target could be a standard Eye Chart that is typically spaced 20 feet from the subject. The goggle unit 10 of the present invention allow such a chart to be present to the subject on the goggle and would allow the operator to perform testing on such a chart without setting up an actual full scale system.

The eye tracking technology is also known in the art, also called video oculography. The camera based eye tracking may use the EYE PORTAL® brand goggle based eye tracking cameras and software available from the assignee of this invention.

The combination of the eye tracking and the display of simulated distanced visual targets allows the unit 10 to automatically run a number of preprogrammed neurologic tests and to record the physiologic responses thereto. Essentially the unit provides a full room sized visual testing platform in a single goggle mounting unit 10.

The rational/purpose of the proposed system is to rapidly assess field-deployed personnel for potential TBI or mTBI. The technician in the field merely needs to put the unit on the subject and run the pre-identified tests. The contemplated system design will incorporate over 15 standard neurological tests simplified for a pass/refer criterion, that will facilitate rehabilitation and the monitoring of recovery and the compensation process. The device will provide a cost effective means to pre-screen soldiers prior to deployment to establish baseline brain function for future comparison if a future mTBI occurs. The device will allow full vestibular diagnostics and VOR rehabilitation for more in depth usage and follow up care.

This portable VR device will consist of: (a) rugged tablet PC, preferably meeting military specifications to provide for rugged use, equipped with software used to control the VR stimuli as well as to collect and analyze eye response data; (b) head mounted goggle with VR display used to present stimuli at the designated simulated distance for the test and integrated binocular eye tracking cameras.

The present invention provides a solution to overcome the limitations of existing screening, diagnostic and rehabilitation methods for mTBI patients. The proposed new system employs portable, head mounted VR eye tracking goggles from field to post-deployment. The system will incorporate efficient clinical diagnostic and screening methodologies for detecting mTBI related vestibular and neurological abnormalities. This technology will be instrumental in pre-screening, diagnosing and monitoring the progression of mTBI in soldiers who are deployed in remote locations, as well as those seeking post-deployment clinical services. Having the ability to collect objective, functional data will aid the clinicians in the diagnosis between mTBI and other psychological disorders.

The present invention uses analytical and 3-D design methods, in the development of anatomically and functionally correct head-mounted goggle that can accommodate existing VR optics and miniature digital cameras. The VR stimulus software is integrated into existing vestibular/neurological software for protocol setup, test results analysis, and to create VR stimulus.

The screening protocols of the googles 10 is anticipated to include the following standard tests horizontal and vertical calibration of subject eyes, nystagmus tests (horizontal, vertical and spontaneous), horizontal and vertical smooth pursuit, horizontal and vertical saccades, optokinetic tests, subjective visual horizontal and vertical and two rehabilitation protocols (exercises), one VOR and second optokinetic.

The invention may include the step of obtaining at step 60 pre-trauma objective physiologic responses of the subject from the head mounted goggle unit based upon each of the visual stimulus presented to the subject, wherein the pre-trauma objective physiologic responses form a baseline for the subject. With a baseline the step of using the objective physiologic responses to diagnose the presence of traumatic brain injury at step 80 includes a determining whether at least one post-trauma objective physiologic responses of the subject differs from the associated pre-trauma objective physiologic response by greater than a preset threshold for that response. Alternatively the invention may utilize a normative database of similar subjects (e.g. all men in their 20s, etc) in place of step 60 whereby the step of using the objective physiologic responses to diagnose the presence of traumatic brain injury at step 80 includes determining whether at least one post-trauma objective physiologic responses of the subject differs from an associated objective physiologic response of a normative database of similar subjects by greater than a preset threshold for that response. The baseline approach is preferred, but may not always be available.

It is understood, therefore, that this invention is not limited to the particular embodiments disclosed, but it is intended to cover modifications that are within the spirit and scope of the invention, as defined by the appended claims and equivalents thereto.

What is claimed is:

1. A method of diagnosis of traumatic brain injury comprising the steps of:
    providing a head mounted goggle based stimulus generating eye tracking unit to the subject;
    presenting visual stimulus to the subject, wherein the visual stimulus is in the head mounted goggle based system and forms the optical target stimulus for at least two distinct tests including at least two of nystagmus tests, smooth pursuit tests, saccades tests, optokinetic tests, subjective visual horizontal and subjective visual vertical;
    obtaining objective physiologic response of the subject from the head mounted goggle unit based upon each of the visual stimulus presented to the subject in each test; and
    using the objective physiologic responses to diagnose the presence of traumatic brain injury.

2. The method of diagnosis of traumatic brain injury according to claim 1, further including the step of obtaining pre-trauma objective physiologic responses of the subject from the head mounted goggle unit based upon each of the visual stimulus presented to the subject, wherein the pre-trauma objective physiologic responses form a baseline for the subject.

3. The method of diagnosis of traumatic brain injury according to claim 2, wherein the step of using the objective physiologic responses to diagnose the presence of traumatic brain injury includes a determining whether at least one post-trauma objective physiologic responses of the subject differs from the associated pre-trauma objective physiologic response by greater than a preset threshold for that response.

4. The method of diagnosis of traumatic brain injury according to claim 3, wherein the visual stimulus presented to the subject includes at least one nystagmus test.

5. The method of diagnosis of traumatic brain injury according to claim 3, wherein the visual stimulus presented to the subject includes at least one horizontal nystagmus test, one vertical and one spontaneous nystagmus test.

6. The method of diagnosis of traumatic brain injury according to claim 3, wherein the visual stimulus presented to the subject includes at least one horizontal smooth pursuit test and at least one vertical smooth pursuit test.

7. The method of diagnosis of traumatic brain injury according to claim 3, wherein the visual stimulus presented to the subject includes at least one horizontal saccades test and at least one vertical saccades test.

8. The method of diagnosis of traumatic brain injury according to claim 1, wherein the step of using the objective physiologic responses to diagnose the presence of traumatic brain injury includes a determining whether at least one post-trauma objective physiologic responses of the subject differs from an associated objective physiologic response of a normative database of similar subjects by greater than a preset threshold for that response.

9. A method of diagnosis of traumatic brain injury comprising the steps of:
    providing a head mounted stimulus generating eye tracking goggle unit coupled to the subject;
    presenting a plurality of visual stimulus to the subject, wherein each visual stimulus is presented in the eye tracking unit, wherein each visual stimulus provides a target stimulus for a distinct visual based neurologic test;
    obtaining objective physiologic response of the subject from the eye tracking unit based upon each of neurologic test associated with each visual stimulus presented to the subject; and
    using the objective physiologic responses to the neurologic tests to diagnose the presence of traumatic brain injury.

10. The method of diagnosis of traumatic brain injury according to claim 9, wherein the visual stimulus presented to the subject includes at least one nystagmus test.

11. The method of diagnosis of traumatic brain injury according to claim 9, wherein the visual stimulus presented to the subject includes at least one horizontal nystagmus test, one vertical and one spontaneous nystagmus test.

12. The method of diagnosis of traumatic brain injury according to claim 9, wherein the visual stimulus presented to the subject includes at least one horizontal smooth pursuit test and at least one vertical smooth pursuit test.

13. The method of diagnosis of traumatic brain injury according to claim 9, wherein the visual stimulus presented to the subject includes at least one horizontal saccades test and at least one vertical saccades test.

14. The method of diagnosis of traumatic brain injury according to claim 9, wherein the step of using the objective physiologic responses to diagnose the presence of traumatic brain injury includes a determining whether at least one post-trauma objective physiologic responses of the subject differs from an associated objective physiologic response of a normative database of similar subjects by greater than a preset threshold for that response.

15. The method of diagnosis of traumatic brain injury according to claim 9, further including the step of obtaining pre-trauma objective physiologic responses of the subject from the head mounted goggle unit based upon each of the visual stimulus presented to the subject, wherein the pre-trauma objective physiologic responses form a baseline for the subject.

16. The method of diagnosis of traumatic brain injury according to claim 15, wherein the step of using the objective physiologic responses to diagnose the presence of traumatic brain injury includes a determining whether at least one post-trauma objective physiologic responses of the subject differs from the associated pre-trauma objective physiologic response by greater than a preset threshold for that response.

17. The method of diagnosis of traumatic brain injury according to claim 16, wherein the visual stimulus presented to the subject includes at least one nystagmus test.

18. The method of diagnosis of traumatic brain injury according to claim 16, wherein the visual stimulus presented to the subject includes at least one horizontal nystagmus test, one vertical and one spontaneous nystagmus test.

19. The method of diagnosis of traumatic brain injury according to claim 17, wherein the visual stimulus presented to the subject includes at least one horizontal smooth pursuit test and at least one vertical smooth pursuit test.

20. The method of diagnosis of traumatic brain injury according to claim 18, wherein the visual stimulus presented to the subject includes at least one horizontal saccades test and at least one vertical saccades test.

* * * * *